United States Patent
Kim et al.

(10) Patent No.: US 12,403,211 B2
(45) Date of Patent: Sep. 2, 2025

(54) ROBOT AND CONTROL METHOD FOR IDENTIFYING A STERILIZATION AREA

(71) Applicant: SAMSUNG ELECTRONICS CO., LTD., Suwon-si (KR)

(72) Inventors: Dohoon Kim, Suwon-si (KR); Yosub Park, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 175 days.

(21) Appl. No.: 18/118,591

(22) Filed: Mar. 7, 2023

(65) Prior Publication Data

US 2023/0201396 A1    Jun. 29, 2023

Related U.S. Application Data

(63) Continuation of application No. PCT/KR2021/011657, filed on Aug. 31, 2021.

(30) Foreign Application Priority Data

Oct. 7, 2020   (KR) .................. 10-2020-0129637

(51) Int. Cl.
*A61L 2/24* (2006.01)
*A61L 2/10* (2006.01)
(Continued)

(52) U.S. Cl.
CPC .................. *A61L 2/24* (2013.01); *A61L 2/10* (2013.01); *A61L 2/18* (2013.01); *G06T 7/70* (2017.01);
(Continued)

(58) Field of Classification Search
CPC ..... A61L 2/10; A61L 2/18; A61L 2/24; A61L 2202/14; A61L 2202/15; A61L 2202/16;
(Continued)

(56) References Cited

U.S. PATENT DOCUMENTS 9,352,469 B2   5/2016   Stewart
11,421,905 B2   8/2022   Takayanagi
(Continued)

FOREIGN PATENT DOCUMENTS

CN   109701060 A   5/2019
CN   111331571 A   6/2020
(Continued)

OTHER PUBLICATIONS

McGuinness K, Morice A, Woodcock A, Smith J. The Leicester Cough Monitor: a semi-automated, semi-validated cough detection system? Eur Respir J. Aug. 2008;32(2):529-30; author reply 530-1. doi: 10.1183/09031936.00052008. Erratum in: Eur Respir J. Jan. 2009;33(1):224. PMID: 18669799.*
(Continued)

*Primary Examiner* — Andrew R Dyer
(74) *Attorney, Agent, or Firm* — Sughrue Mion, PLLC

(57) ABSTRACT

Provided is a robot comprising a driving part, a camera, a plurality of microphones arranged in different directions. The robot further comprises a memory storing instructions, and a processor configured to execute the instructions to identify an originating direction of an audio signal input through the plurality of microphones based on the audio signal being identified as corresponding to a coughing sound, control the camera to capture an image in the originating direction, identify a sterilization area based on a position of a user who does not wear a mask identified in the image, and control the driving part to move the robot to the sterilization area.

21 Claims, 14 Drawing Sheets

(51) Int. Cl.

| | |
|---|---|
| *A61L 2/18* | (2006.01) |
| *G06T 7/70* | (2017.01) |
| *G06V 10/82* | (2022.01) |
| *G06V 20/50* | (2022.01) |
| *G06V 40/10* | (2022.01) |
| *G10L 25/30* | (2013.01) |
| *G10L 25/66* | (2013.01) |
| *H04N 7/18* | (2006.01) |
| *H04N 23/695* | (2023.01) |
| *H04R 1/40* | (2006.01) |
| *H04R 3/00* | (2006.01) |

(52) U.S. Cl.
CPC .............. *G06V 10/82* (2022.01); *G06V 20/50* (2022.01); *G06V 40/10* (2022.01); *G10L 25/30* (2013.01); *G10L 25/66* (2013.01); *H04N 7/188* (2013.01); *H04N 23/695* (2023.01); *H04R 1/406* (2013.01); *H04R 3/005* (2013.01); *A61L 2202/14* (2013.01); *A61L 2202/16* (2013.01); *G06T 2207/20084* (2013.01); *G06T 2207/30196* (2013.01)

(58) Field of Classification Search
CPC .......... A61L 2202/25; A61L 9/14; A61L 9/00; B25J 11/00; B25J 11/0085; B25J 13/00; B25J 13/003; B25J 19/02; B25J 19/023; B25J 9/00; B25J 9/0009; B25J 9/16; B25J 9/161; B25J 9/1679; B25J 9/1697; G05D 1/0088; G05D 1/0246; G05D 1/0255; G06T 2207/20084; G06T 2207/30196; G06T 7/70; G06V 10/82; G06V 20/50; G06V 20/52; G06V 40/10; G06V 40/103; G06V 40/16; G10L 25/30; G10L 25/66; H04N 23/60; H04N 23/695; H04N 7/183; H04N 7/188; H04R 1/028; H04R 1/406; H04R 2430/20; H04R 3/005
USPC ......................................................... 701/25
See application file for complete search history.

(56) References Cited

U.S. PATENT DOCUMENTS

| | | | |
|---|---|---|---|
| 11,763,366 B1* | 9/2023 | Derza ...................... G06N 3/08 | 705/26.41 |
| 12,087,284 B1* | 9/2024 | Lezzoum ................ G06F 3/165 | |
| 2007/0209143 A1 | 9/2007 | Choi et al. | |
| 2019/0213438 A1 | 7/2019 | Jones et al. | |
| 2020/0046302 A1* | 2/2020 | Jacquel ................... A61B 5/091 | |
| 2020/0168339 A1* | 5/2020 | Correnti ................. G16H 50/30 | |
| 2020/0393159 A1 | 12/2020 | Takayanagi | |
| 2021/0027893 A1* | 1/2021 | Nematihosseinabadi ................ G16H 10/60 | |
| 2021/0287792 A1* | 9/2021 | Fan ......................... G16H 40/63 | |
| 2021/0353785 A1* | 11/2021 | Bonutti .................... C02F 1/32 | |
| 2022/0047209 A1* | 2/2022 | Shin ..................... G06V 10/778 | |
| 2022/0355481 A1* | 11/2022 | Jo .......................... A47L 9/2805 | |
| 2022/0359069 A1* | 11/2022 | Miyazawa ............. G16H 10/60 | |
| 2022/0364758 A1 | 11/2022 | Takayanagi | |
| 2022/0387641 A1* | 12/2022 | Daczko ..................... A61L 2/10 | |
| 2022/0409089 A1* | 12/2022 | den Brinker ........... G16H 50/20 | |
| 2023/0120290 A1* | 4/2023 | Baarman ................ G16H 10/65 | 15/3 |
| 2023/0149581 A1* | 5/2023 | Barfett ...................... A61L 2/10 | 422/2 |

FOREIGN PATENT DOCUMENTS

| | | |
|---|---|---|
| CN | 111358990 A | 7/2020 |
| CN | 111376268 A | 7/2020 |
| JP | 2017-169613 A | 9/2017 |
| KR | 10-0695172 B1 | 3/2007 |
| KR | 10-1742489 B1 | 6/2017 |
| KR | 10-2017-0139354 A | 12/2017 |
| KR | 10-2018-0079824 A | 7/2018 |
| KR | 10-2019-0065569 A | 6/2019 |
| KR | 10-2156511 B1 | 9/2020 |
| WO | 2019239812 A1 | 12/2019 |

OTHER PUBLICATIONS

Seher Asaf, "Hong Kong Airport is using virus-killing robots to disinfect public areas," https://www.businesstraveller.com/business-travel/2020/04/05/hong-kong-airport-is-using-virus-killing-robots-to-disinfect-public-areas/, Apr. 5, 2020, 4 Total Pages.

"Denmark's robotic medical devices are making great strides amid COVID-19," https://dream.kotra.or.kr/kotranews/cms/news/actionKotraBoardDetail.do?SITE_NO=3&MENU_ID=180&CONTENTS_NO=1&bbsGbn=243&bbsSn=243&pNttSn=183011, Jun. 30, 2020, 10 total pages.

"Explosive growth of China;s robot industry expected," https://www.newspim.com/news/view/20200224001040, Feb. 2020, 9 total pages.

Kim Eung-min, "In the post-corona era, 'robots' are on the rise," https://www.pharmnews.com/news/articleView.html?idxno=100482, May 14, 2020.

International Search Report (PCT/ISA/210) issued by the International Searching Authority on Nov. 29, 2021 in corresponding International Application No. PCT/KR2021/011657.

* cited by examiner

FIG. 6

| | LOCATION 610 | STERILIZATION AREA SCALE 620 | STERILIZATION INTENSITY 630 |
|---|---|---|---|
| 611 | HALLWAY | LARGE | LOW |
| 612 | BATHROOM | MEDIUM | MEDIUM |
| 613 | ENTRANCE DOOR | SMALL | MEDIUM |
| 614 | DRINKING FOUNTAIN | SMALL | HIGH | ular
ROBOT AND CONTROL METHOD FOR IDENTIFYING A STERILIZATION AREA

CROSS-REFERENCE TO RELATED APPLICATIONS

This application is a bypass continuation of PCT International Application No. PCT/KR2021/011657, which was filed on Aug. 31, 2021, and claims priority to Korean Patent Application No. 10-2020-0129637, filed on Oct. 7, 2020, in the Korean Intellectual Property Office, the disclosures of which are incorporated herein by reference in their entireties.

BACKGROUND

1. Field

The disclosure relates to a robot that performs a sterilization function and a control method thereof.

2. Description of Related Art

Preventing infections of contagious diseases (e.g., the highly contagious Coronavirus disease) is an important social issue. One way that an individual is infected by a virus is through droplet spraying via coughing or contact, but because sterilization robots of related art sterilize a droplet spraying point or a contact point through a user operation, there is difficulty in performing an automated sterilization function.

SUMMARY

Provided is a robot which can identify a sterilization area on its own without user operation, and a control method thereof. According to the various embodiments of the disclosure, areas that require sterilization may be sterilized with only the robot and without using other sensors installed in an indoor space.

According to an aspect of the disclosure, a robot includes: a driving part; a camera; a plurality of microphones arranged in different directions; a memory storing instructions; and a processor configured to execute the instructions to: based on an audio signal input through the plurality of microphones being identified as corresponding to a coughing sound, identify an originating direction of the audio signal, control the camera to capture an image in the originating direction, identify a sterilization area based on a position of a non-mask wearing user identified from the image, and control the driving part to move to the sterilization area.

The processor may be further configured to execute the instructions to: identify the sterilization area based on the position of the user and a threshold range corresponding to an intensity of the audio signal.

The processor may be further configured to execute the instructions to: determine a scale of the sterilization area based on a number of non-mask wearing users identified from the image.

The processor may be further configured to execute the instructions to: identify the sterilization area based on a plurality of positions corresponding to a plurality of non-mask wearing user identified from the image of the respective users.

The processor may be further configured to execute the instructions to: determine at least one of a scale of the sterilization area, and a sterilization intensity, based on whether the position of the user may be within a pre-set area.

The pre-set area may include at least one of an area including an object with high contact frequency by users, an area with high visiting frequency by users, and an area with low mask wearing frequency by users.

The processor may be further configured to execute the instructions to: identify whether the audio signal corresponds to the coughing sound by using a first neural network model trained to identify whether the audio signal comprises a coughing sound.

The processor may be further configured to execute the instructions to: identify whether the image comprises a non-mask wearing user by using a second neural network model trained to identify whether the image comprises a non-mask wearing user.

The robot may further include a distance sensor, and the processor may be further configured to execute the instructions to: based on a plurality of sterilization areas being identified, identify a direction and a distance with respect to each sterilization area using the distance sensor, and set a traveling route for a sterilization operation based on the direction and distance to each sterilization area.

The robot may further include a sterilization device configured to perform a sterilization function, and the processor may be further configured to execute the instructions to: control the sterilization device to perform the sterilization function, based on the robot having moved to the sterilization area.

According to an aspect of the disclosure, a method of controlling a robot includes: based on an audio signal input through a plurality of microphones on the robot being identified as corresponding to a coughing sound, identifying an originating direction of the audio signal based on an arrangement direction of each microphone; capturing an image in the originating direction of the audio signal using a camera on the robot; identifying a sterilization area based on a position of a non-mask wearing user identified from the image; and moving the robot to the sterilization area.

The sterilization area may be identified based on the position of the user and a threshold range corresponding to an intensity of the audio signal.

The identifying the sterilization area may include: determining a scale of the sterilization area based on a number of non-mask wearing users identified from the image.

The sterilization may be identified based on a plurality of positions corresponding to a plurality of non-mask wearing users identified from the image.

The identifying the sterilization area may include: determining at least one of a scale of the sterilization area, and a sterilization intensity, based on whether the position of the user is within a pre-set area.

According to an aspect of the disclosure, a non-transitory computer readable medium stores computer readable program code or instructions which are executable by a processor to perform a method of controlling a robot. The method includes: based on an audio signal input through a plurality of microphones on the robot being identified as corresponding to a coughing sound, identifying an originating direction of the audio signal based on an arrangement direction of each microphone; capturing an image in the originating direction of the audio signal using a camera on the robot; and identifying a sterilization area based on a position of a non-mask wearing user identified from the image; and moving the robot to the sterilization area.

The identifying the sterilization area may include: identifying the sterilization area based on the position of the user and a threshold range corresponding to an intensity of the audio signal.

The identifying the sterilization area may include: determining a scale of the sterilization area based on a number of non-mask wearing users identified from the image.

The identifying the sterilization area may include: identifying the sterilization area based on a plurality of positions corresponding to a plurality of non-mask wearing users identified from the image.

The identifying the sterilization area may include: determining at least one of a scale of the sterilization area, and a sterilization intensity, based on whether the position of the user is within a pre-set area.

BRIEF DESCRIPTION OF THE DRAWINGS

The above and other aspects, features, and advantages of certain embodiments of the present disclosure will be more apparent from the following description taken in conjunction with the accompanying drawings, in which:

FIG. 6 illustrates a scale of a sterilization area that corresponds to a location included with a sterilization point and a sterilization intensity according to an embodiment;

DETAILED DESCRIPTION

Figure 1:
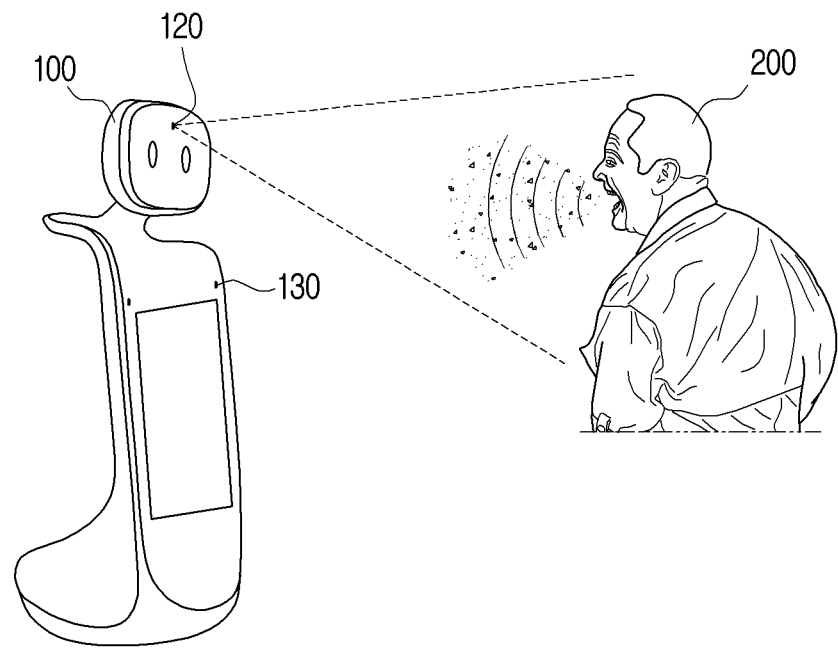
FIG. 1 is a diagram illustrating an operation method of a robot according to an embodiment.

Hereinafter, embodiments of the present disclosure will be described in detail with reference to the accompanying drawings, where similar reference characters denote corresponding features consistently throughout.

Terms used in describing various embodiments of the disclosure are general terms selected that are currently widely used considering their function herein. However, the terms may change depending on intention, legal or technical interpretation, emergence of new technologies, and the like of those skilled in the related art. Further, in certain cases, there may be terms arbitrarily selected, and in this case, the meaning of the term will be disclosed in greater detail in the corresponding description. Accordingly, the terms used herein are not to be understood simply as its designation but based on the meaning of the term and the overall context of the disclosure.

In the disclosure, expressions such as "have," "may have," "include," "may include," or the like are used to designate a presence of a corresponding characteristic (e.g., elements such as numerical value, function, operation, or component), and not to preclude a presence or a possibility of additional characteristics.

The expression at least one of A and/or B is to be understood as indicating any one of "A" or "B" or "A and B."

Expressions such as "first," "second," "1st," "2nd," and so on used herein may be used to refer to various elements regardless of order and/or importance. Further, it should be noted that the expressions are merely used to distinguish an element from another element and not to limit the relevant elements.

When a certain element (e.g., first element) is indicated as being "(operatively or communicatively) coupled with/to" or "connected to" another element (e.g., second element), it may be understood as the certain element being directly coupled with/to the another element or as being coupled through other element (e.g., third element).

A singular expression includes a plural expression, unless otherwise specified. It is to be understood that the terms such as "consist" or "include" are used herein to designate a presence of a characteristic, number, step, operation, element, component, or a combination thereof, and not to preclude a presence or a possibility of adding one or more of other characteristics, numbers, steps, operations, elements, components or a combination thereof.

The term "module" or "part" used in the embodiments herein perform at least one function or operation, and may be implemented with a hardware or software, or implemented with a combination of hardware and software. Further, a plurality of "modules" or a plurality of "parts," except for a "module" or a "part" which needs to be implemented to a specific hardware, may be integrated to at least one module and implemented in at least one processor.

In the disclosure, the term "user" may refer to a person using an electronic device or a device (e.g., artificial intelligence electronic device) using an electronic device.

FIG. 1 is a diagram illustrating an operation method of a robot according to an embodiment of the disclosure.

Generally, a spread of a virus may occur through droplet spraying or contacting a contaminated point, but in FIG. 1, a function of a robot 100 will be described assuming that a sterilization operation of preventing the spread of virus via droplet spraying caused by coughing is to be performed. A camera provided in the robot 100 according to an embodiment may have a certain field of view. In this case, the camera 120 may not detect coughing events occurring from all directions.

The robot 100 according to an embodiment may include a plurality of microphones 130. If an audio signal corresponding to a coughing sound is input through the plurality of microphones 130, the robot may identify a direction from which the audio signal is originated. Then, the robot 100 may control the camera 120 to capture the direction from which the coughing event occurred. In this process, a camera module itself may be rotated to capture the direction from which the coughing event occurred, but the robot 100 itself may be rotated using a driving part 110 included in the robot 100 to capture the direction from which the coughing event occurred.

The robot 100 may identify whether a non-mask wearing user 200 is present in an image which captured the direction from which the coughing event occurred, and move to a point at which the non-mask wearing user 200 is positioned.

Various embodiments of identifying areas that require sterilization without a separate sensor provided in an indoor space or user operation will be described below.

Figure 2:
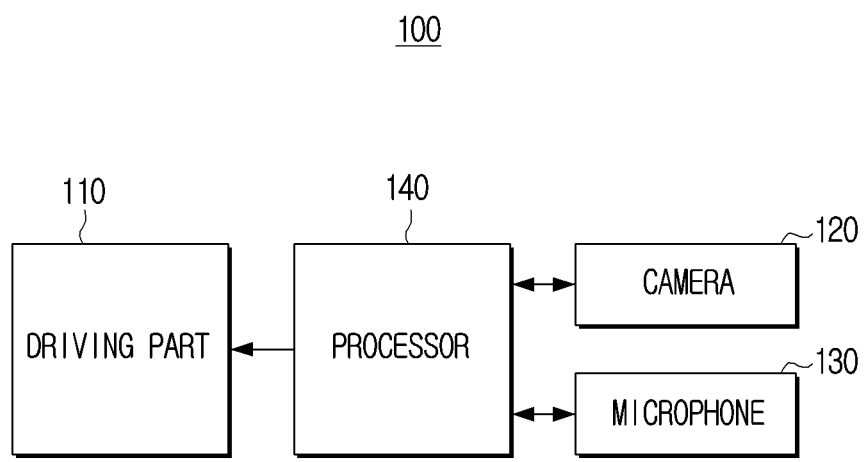
FIG. 2 is a block diagram illustrating a configuration of a robot according to an embodiment.

FIG. 2 is a block diagram illustrating a configuration of a robot according to an embodiment of the disclosure.

Referring to FIG. 2, the robot 100 according to an embodiment of the disclosure may include a driving part 110, a camera 120, a microphone 130, and a processor 140.

The driving part 110 may be a device which can travel the robot 100, and the driving part 100 may adjust a traveling direction and traveling speed according to a control of the processor 140. To this end, the driving part 110 may include a power generating device which generates power for the robot 100 to travel (e.g., gasoline engine, diesel engine, liquefied petroleum gas (LPG) engine, electric motor, etc. according to fuel used (or energy source)), a steering device for adjusting a traveling direction (e.g., manual steering, hydraulics steering, electronic control power steering (EPS), etc.), a travelling device which travels the robot 100 according to power (e.g., wheel, propeller, etc.), and the like. Here, the driving part 110 may be modified and realized according to a traveling type (e.g., wheel type, walking type, flying type, etc.) of the robot 100.

The camera 120 may obtain an image by performing capturing of an area within the field of view (FoV) of the camera.

The camera 120 may include a lens which focuses on an object, for example, visible rays or signals that are reflected by the user and received to an image sensor and an image sensor which can detect visible rays or signals. Here, the image sensor may include 2-dimensional (2D) pixel arrays which area divided into a plurality of pixels. The camera 120 according to an embodiment may be implemented as a depth camera.

The microphone 130 may be a configuration which can receive audio signals. Audio signals which may be received through the microphone 130 may be sounds of an audible frequency band or a non-audible frequency band. Sounds of an audible frequency band may be having a frequency of sound that is audible to a person, and may be a sound between 20 Hz and 20 KHz. In addition, sounds of a non-audible frequency band may be having a frequency of sound that is not audible to a person, and may be a sound between 10 kHz to 300 GHz. Here, the audio signal may be a sound that corresponds to a coughing sound, and the microphone 130 according to an embodiment may be configured of the plurality of microphones arranged in different directions.

The processor 140 may control the overall operation of the robot 100. Specifically, the processor 140 may be coupled with each configuration of the robot 100 and control the overall operation of the robot 100. For example, the processor 140 may be coupled with the driving part 110, the camera 120, and the microphone 130 and control the operation of the robot 100.

According to an embodiment, the processor 140 may be designated to various designations such as, for example, and without limitation, a digital signal processor (DSP), a microprocessor, a central processing unit (CPU), a micro controller unit (MCU), a micro processing unit (MPU), a neural processing unit (NPU), a controller, an application processor (AP), and the like, but is described as the processor 140 in the disclosure. The processor 140 may be implemented as a System on Chip (SoC) and a large scale integration (LSI), and may be implemented in a form of a field programmable gate array (FPGA). In addition, the processor 140 may include a volatile memory such as SRAM.

The processor 140 according to an embodiment may identify an originating direction of an audio signal when the audio signal input through the plurality of microphones is identified as an audio signal corresponding to a coughing sound.

Here, the processor 140 may use a neural network model which can be stored in a memory or downloaded from an external server to identify whether the input audio signal is an audio signal that corresponds to a coughing sound. In addition, an audio signal may be identified as corresponding to a coughing sound based on a ratio to which a signal having a specific frequency is included in the audio signal input through the microphone 130.

In order for the processor 140 to identify a direction from which the audio signal corresponding to a coughing sound originated, the microphone 130 may be configured of the plurality of microphones arranged in different directions. The processor 140 may identify an originating direction of an audio signal based on a difference in intensity of audio signals that are respectively input to the plurality of microphones arranged in difference directions.

Then, the processor 140 may control the camera 120 to capture a direction identified as the originating direction of the audio signal that corresponds to the coughing sound. Specifically, the processor 140 may adjust a direction of the camera such that the originating direction of the audio signal is included in the field of view of the camera 120.

The processor 140 may identify a sterilization area based on a position of a user when a non-mask wearing user is identified in an image obtained through the camera 120.

In an example, the processor 140 may use a neural network model which is stored in a memory or downloaded from an external server to identify whether non-mask wearers are included in the obtained image. In another example, the processor 140 may identify whether non-mask wearers are included in the image by directly analyzing the image and identifying an object corresponding to a mask. For example, the processor 140 may identify whether non-mask wearers are included in the image by identifying an object corresponding to a mask based on various feature information, such as, for example, and without limitation, edge information, color information, shape information, and the like, included in the image.

The processor 140 may identify an area that requires sterilization (hereinafter, referred to as 'sterilization area') based on a position of a non-mask wearing user. In the disclosure, when a robot performs a sterilization function to prevent the spread of virus through droplet spraying, positions of non-mask wearers may be described through the term 'sterilization point.'

The processor 140 may identify a sterilization area of a pre-set range based on a sterilization point, and control the driving part 110 for the robot 100 to move to the identified sterilization area.

According to an example, the processor 140 may identify a range that is pre-set based on a sterilization point as a sterilization area based on an intensity of an audio signal. For example, the processor 140 may identify a first threshold distance range based on a sterilization point as a sterilization area if an intensity of an audio signal is less than a threshold intensity, and identify a second threshold distance range which is greater than a first threshold distance based on the sterilization point if the intensity of the audio signal is greater than or equal to the threshold intensity.

According to another example, the processor 140 may identify a sterilization area based on a number of non-mask wearers included in an image captured through the camera 120. For example, the processor 140 may identify the first threshold distance range based on the sterilization point as the sterilization area if the number of non-mask wearers is less than a threshold number, and identify the second threshold distance range which is greater than the first threshold distance based on the sterilization point as the sterilization area based on the number of non-mask wearers being greater than or equal to the threshold number.

According to another example, the processor 140 may identify, based on a plurality of non-mask wearing users being identified, a plurality of sterilization areas based on the positions of the respective users.

In addition, the processor 140 may determine at least one of a scale of a sterilization area or a sterilization intensity based on whether a position at which a non-mask wearing user is identified is within a pre-set area.

Here, the pre-set area may include at least one of an area in which an object with high contact frequency by users is positioned, an area with high visiting frequency by users, and an area with low mask wearing frequency by users.

According to an embodiment of the disclosure, the processor 140 may control the camera 120 to periodically capture all direction of a space in which the robot 100 is positioned, and identify a position distribution and a mask wearing ratio of users in an image that captured all directions of a space. Then, the processor 140 may periodically sterilize an indoor space based on the position distribution and the mask wearing ratio of users.

Here, the robot 100 may perform a sterilization function at every first period on at least one of an area in which a position distribution value of users exceeds a threshold value, and an area in which a ratio of non-mask wearing people exceeds a threshold ratio.

On the other hand, the robot 100 may perform the sterilization function at every second period on at least one of an area in which the position distribution value of users is less than or equal to the threshold value, and an area in which the ratio of non-mask wearing people is less than or equal to the threshold ratio. Here, the first period may be shorter than the second period.

In an example, the processor 140 may identify whether an input audio signal is an audio signal corresponding to a coughing sound by using a first neural network model. Here, the first neural network model may be a model trained to identify whether the input audio signal includes the coughing sound, and the first neural network model may be stored in a memory which is a configuration of the robot 100 or downloaded from an external server. In this case, the first neural network model may be updated periodically or when an event occurs.

In addition, the processor 140 may identify whether an obtained image includes non-mask wearing users by using a second neural network model. Here, the second neural network model may be a model trained to identify whether non-mask wearing users are included in the input image, and the second neural network model may be stored in a memory which is a configuration of the robot 100 or downloaded from an external server. In this case, the first neural network model may be updated periodically or when an event occurs.

In addition, the robot 100 according to an embodiment of the disclosure may further include a distance sensor, and the processor 140 may identify, based on a plurality of sterilization areas being identified, a direction and distance of the respective sterilization areas using the distance sensor, and set a travelling for a sterilization operation based on the identified direction and distance. For example, the distance sensor may be implemented as a LIDAR sensor, a depth camera, and the like.

In addition, the robot 100 according to an embodiment of the disclosure may further include a sterilization device, and the processor 140 may control the sterilization device to perform a sterilization function when the robot 100 is moved to an identified sterilization area.

Figure 3A:
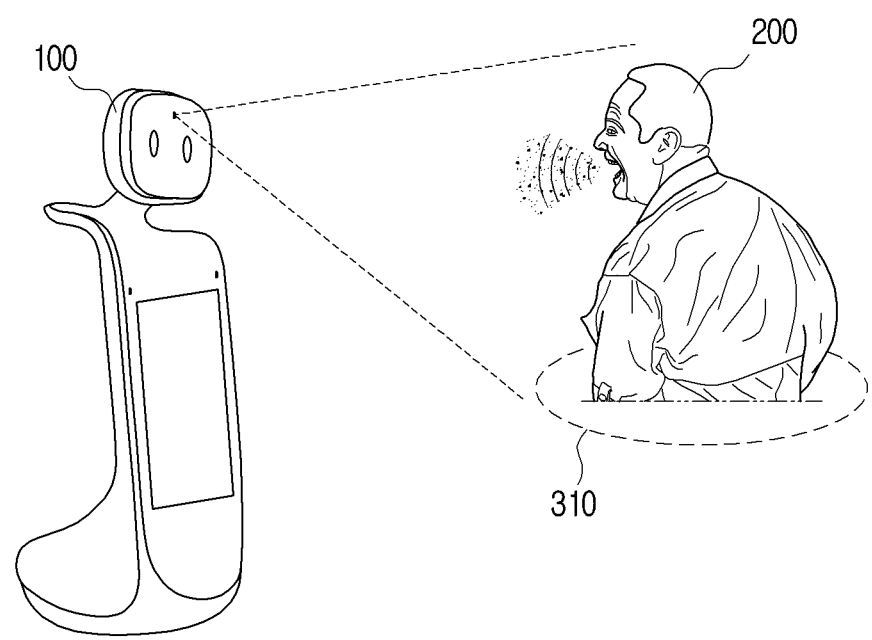
FIG. 3A and FIG. 3B illustrate a scale of a sterilization area that corresponds to an intensity of a coughing sound according to an embodiment.
Figure 3B:
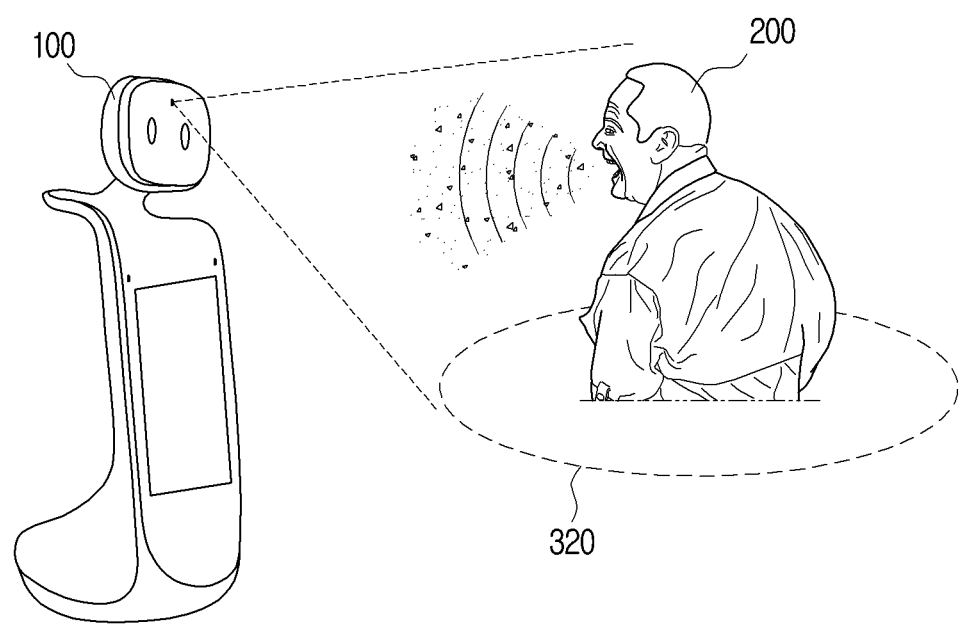

FIG. 3A and FIG. 3B illustrate a scale of a sterilization area that corresponds to an intensity of a coughing sound according to an embodiment of the disclosure.

The processor 140 according to an embodiment of the disclosure may determine the scale of the sterilization area based on an intensity of an audio signal corresponding to the coughing sound.

As there are more non-mask wearing users, there is also a tendency of coughing sounds becoming louder as the intensity of coughing becomes greater, and a spread of droplet spraying may occur actively at the same time. Accordingly, the processor 140 may determine the scale of the sterilization area as large as the intensity of the audio signal corresponding to the coughing sound increases.

Specifically, the processor 140 may identify an area of a threshold range based on a position of a non-mask wearing user as a sterilization area based on the intensity of the audio signal corresponding to the coughing sound, and the processor 140 may identify an area of a large threshold range as the sterilization area as the intensity of the audio signal increases.

Referring to FIG. 3A, the user 200 may perform slight coughs (hereinafter, a first coughing) which generates a small sound. In an example, the robot 100 may identify an intensity of an audio signal corresponding to a first coughing sound, and identify an area 310 of a first threshold range based on a position of the user 200 as a sterilization area.

Referring to FIG. 3B, the user 200 may perform coughing (hereinafter, a second coughing) which generates a loud sound. The second coughing may include not only common coughing but also sneezing. The robot 100 according to an example may identify an intensity of an audio signal corresponding to a second coughing sound, and identify an area 320 of a second threshold range based on a position of the user 200 as a sterilization area. Here, the first threshold range may have a value smaller than the second threshold range.

According to an embodiment, the processor 140 may identify not only the intensity of the audio signal corresponding to the coughing sound, but also a sterilization area based on a frequency of the coughing sound included in the audio signal.

Figure 4A:
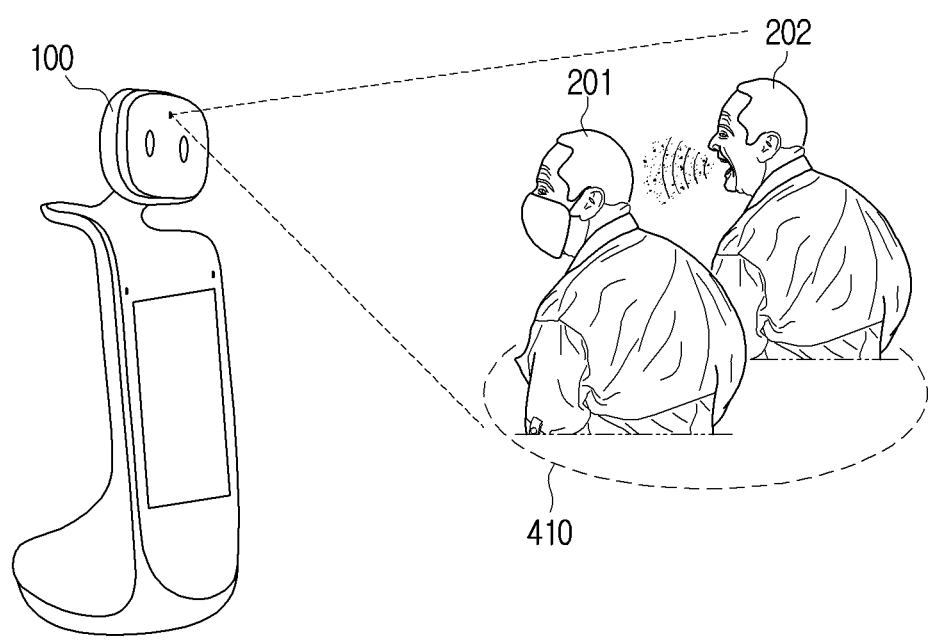
FIG. 4A and FIG. 4B illustrate a scale of a sterilization area that corresponds to a number of non-mask wearers according to an embodiment.
Figure 4B:
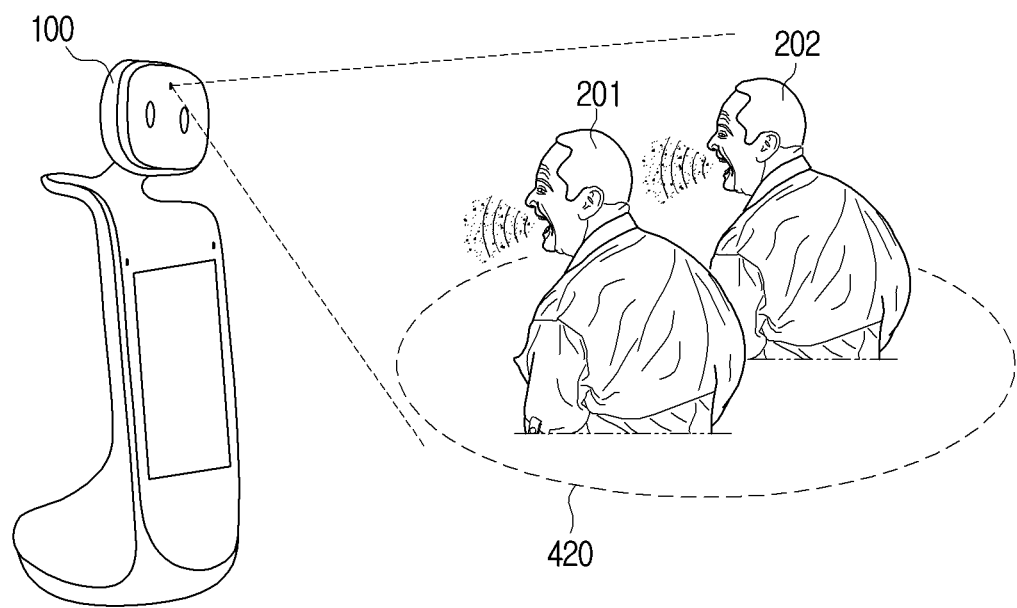

FIG. 4A and FIG. 4B illustrate a scale of a sterilization area that corresponds to a number of non-mask wearers according to an embodiment of the disclosure.

The processor 140 according to an embodiment of the disclosure may determine a scale of a sterilization area based on a number of non-mask wearing users of the users included in the image obtained through the camera 120.

If there is a plurality of users present within the field of view of the camera 120, the spread of droplet spraying by coughing may occur actively as there are more non-mask wearing users. In addition, because uninfected people may be included among the non-mask wearing users, it may be necessary for an area that requires sterilization to be set more widely. Accordingly, the processor 140 may determine the scale of the sterilization area as large as there are more number of non-mask wearing users.

Referring to FIG. 4A, in the field of view of the camera 120, a mask wearing user 201 and a non-mask wearing user 202 may be included. In this case, the processor 140 may identify a number of non-mask wearing user as one person, and identify a first sterilization area 410 corresponding thereto.

Referring to FIG. 4B, a plurality of non-mask wearing users 201 and 202 may be included. In this case, the processor 140 may identify the number of non-mask wearing users as two persons, and identify a second sterilization area 420 corresponding thereto. Here, the second sterilization area may include an area of a wider range than the first sterilization area.

Figure 5A:
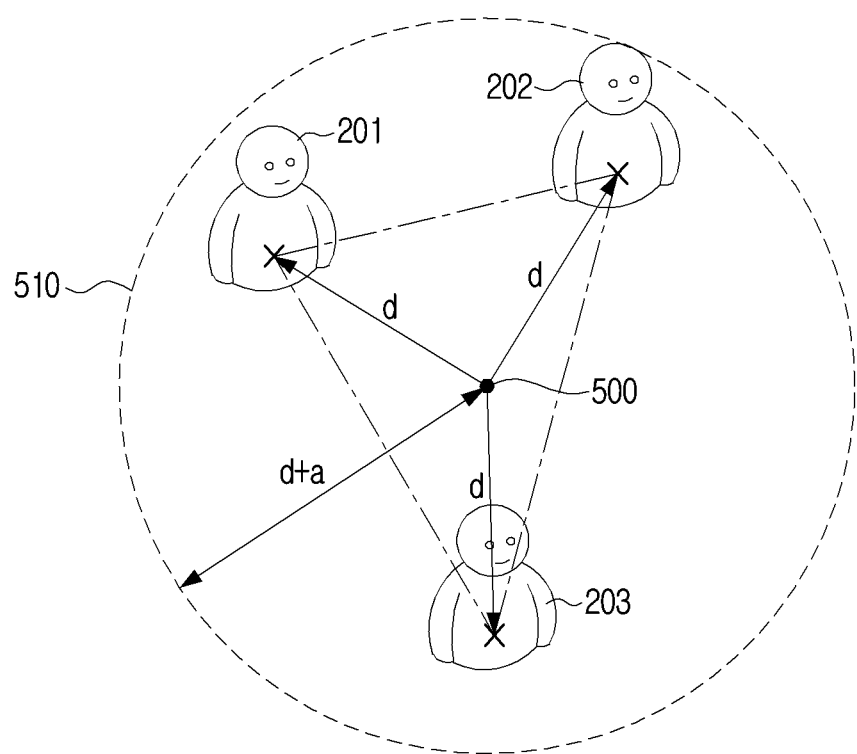
FIG. 5A and FIG. 5B are diagrams illustrating a method of determining a sterilization area for sterilizing a plurality of sterilization points according to an embodiment.
Figure 5B:
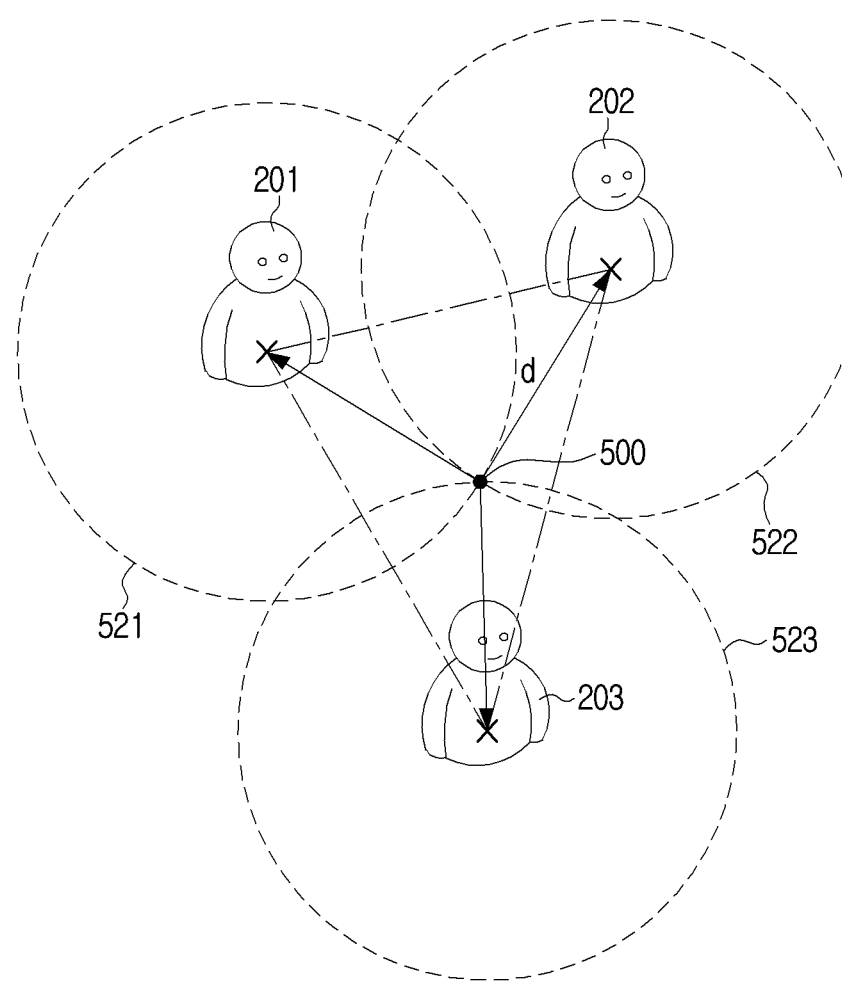

FIG. 5A and FIG. 5B are diagrams illustrating a method of determining a sterilization area for sterilizing a plurality of sterilization points according to an embodiment of the disclosure.

The processor 140 according to an embodiment of the disclosure may determine, based on a plurality of non-mask wearing users 201, 202, and 203 being identified, a sterilization area with various methods. Specifically, the processor 140 may identify the positions of the respective non-mask wearers included in the images which captured the direction from which a plurality of coughing events is identified as separate sterilization points, and identify a sterilization area based on the identified sterilization points.

Referring to FIG. 5A, the processor 140 according to an example may identify a point 500 (hereinafter, a reference point) that is spaced apart by a same distance d from the plurality of non-mask wearing users 201, 202, and 203. The processor 140 may identify a circular area which is centered on the reference point 500 to identify a sterilization area that includes all of the plurality of non-mask wearing users 201, 202, and 203, and has a radius of d+a in which a pre-set value a is added to a distance d from the reference point 500 to each user as the sterilization area.

If the number of non-mask wearing users exceeds three persons, the above-described reference point 500 may be determined based on an initial three users with whom the coughing event is identified.

Referring to FIG. 5B, the processor 140 according to an example may identify an area of a threshold range based on the positions of the respective non-mask wearing users 202, 202, and 203 as a sterilization area. For example, the processor 140 may identify a circular area which is centered on the positions of the respective non-mask wearing users 202, 202, and 203, and has a radius of d which is the distance from the reference point 500 to each user as the sterilization areas.

Here, if a new coughing event occurs after the robot 100 performs a sterilization function of the identified sterilization area, the robot 100 may identify a new reference point 500 and additionally identify a new sterilization area based therefrom.

FIG. 6 illustrates a scale of a sterilization area that corresponds to a location included with a sterilization point and a sterilization intensity according to an embodiment of the disclosure.

Specifically, the processor 140 according to an embodiment of the disclosure may identify a sterilization area scale 620 and a sterilization intensity 630 based on a location 610 included with the sterilization point at which the coughing event is identified.

In an example, if the sterilization point identified by the processor 140 is a hallway 611, because the hallway 611 is a location at which a continuous traffic of users occurs, the processor 140 may identify the sterilization area scale 620 as 'large.' The processor 140 may identify the sterilization intensity 630 as 'low' for the hallway 611 in that a user may spend a short time at one point and that there is a low possibility of infection through object contacting.

In another example, if the sterilization point identified by the processor 140 is a bathroom 612, the processor may identify the sterilization area scale 620 as 'medium' because the bathroom 612 is a location through which droplet spraying may be spread due to facilities such as a toilet seat, a urinal, and a bathroom sink. The processor 140 may identify the sterilization intensity 630 as 'medium' in that the bathroom 612 has a relatively high possibility of infection through object contacting.

In another example, if the sterilization point identified by the processor 140 is an entrance door 613, the processor 140 may identify the sterilization area scale 620 as 'small' because the entrance door 613 blocks the spread of droplet spraying between both spaces that are divided by the entrance door 613 as a boundary. The processor 140 may identify the sterilization intensity 630 as 'medium' in that the entrance door 613 has a relatively high possibility of infection through object contacting.

Lastly, if the sterilization point identified by the processor 140 is a drinking fountain 614, the processor 140 may identify the sterilization area scale 620 as 'small' because only an area included within a threshold range from a point at which the drinking fountain 614 is positioned needs to be sterilized. The processor 140 may identify the sterilization intensity 630 as 'high' in that drinking fountain 614 includes a facility which is used by users not wearing a mask and has a noticeably high possibility of infection through object contacting. Here, high, medium, and low are merely classifications according to an example, and the scale of the sterilization area and the sterilization intensity may be classified to various levels.

As described in the above, the robot 100 may perform an optimal sterilization function that corresponds to separate locations through determining the scale of the sterilization area and the sterilization intensity according to various embodiments of the disclosure.

Figure 7A:
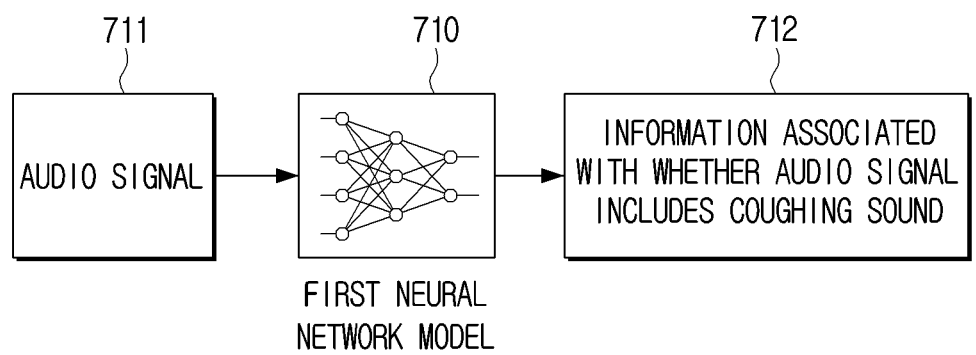
FIG. 7A is a diagram illustrating a method of processing an audio signal through a neural network model according to an embodiment.

FIG. 7A is a diagram illustrating a method of processing an audio signal through a neural network model according to an embodiment of the disclosure.

The processor 140 according to an embodiment of the disclosure may identify whether the audio signal input through the microphone 130 is an audio signal corresponding to a coughing sound by using the first neural network model. Specifically, the processor 140 may input an input audio signal 711 to a first neural network model 710 and obtain information associated with whether the audio signal includes the coughing sound 712.

Here, the first neural network model may be a model trained to identify whether the input audio signal 711 includes the coughing sound. In addition, the first neural network model may be a model trained to identify a type of the coughing sound and a number of users that generated the coughing sound included in the audio signal.

Figure 7B:
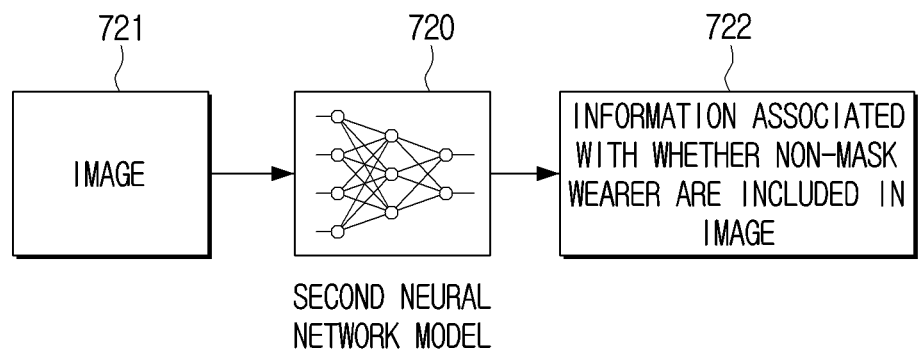
FIG. 7B is a diagram illustrating a method of processing an image through a neural network model according to an embodiment.

FIG. 7B is a diagram illustrating a method of processing an image through a neural network model according to an embodiment of the disclosure.

The processor 140 according to an embodiment of the disclosure may identify whether non-mask wearers are included in an image obtained through the camera 120 by using the second neural network model. Specifically, the processor 140 may input an obtained image 721 to a second neural network model 720 and obtain information associated with whether non-mask wearers are included in the image 722.

Here, the second neural network model may be a model trained to identify whether non-mask wearing users are included in the obtained image 721. With recent demand for masks increasing, masks of various designs are being manufactured and distributed. The processor 140 according to an embodiment of the disclosure may use the second neural network model 720 to accurately identify mask wearing users and non-mask wearing users.

Figure 8:
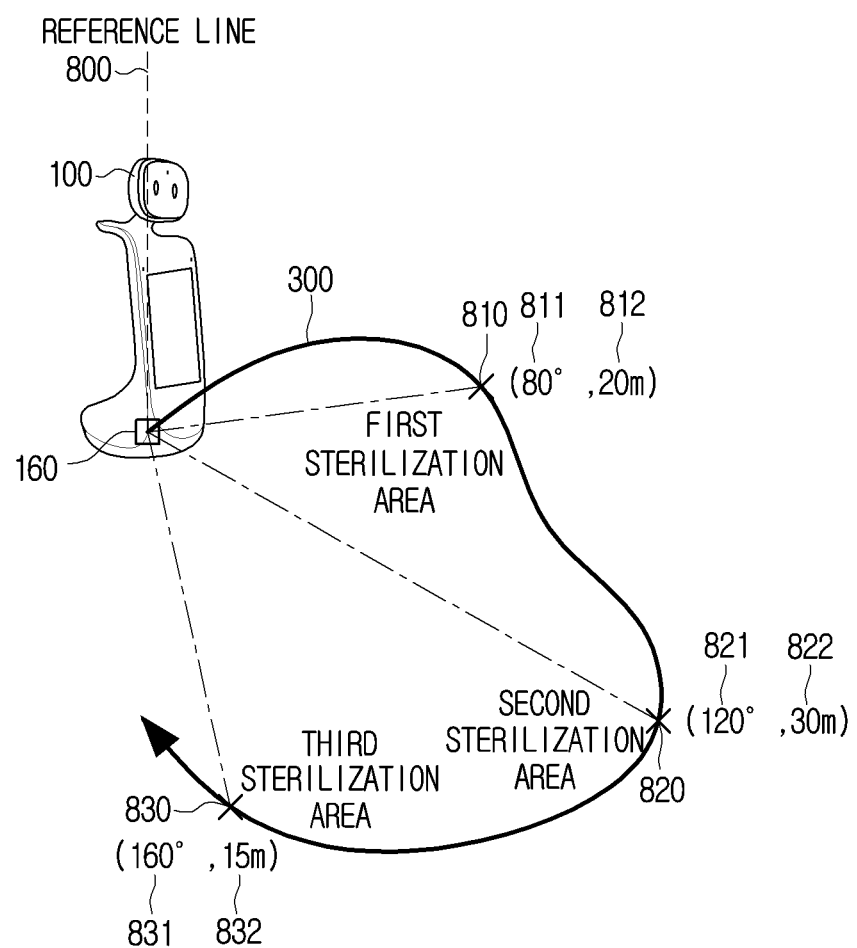
FIG. 8 is a diagram illustrating a traveling route for sterilizing a plurality of sterilization areas according to an embodiment.

FIG. 8 is a diagram illustrating a traveling route for sterilizing a plurality of sterilization areas according to an embodiment of the disclosure.

The robot 100 according to an embodiment of the disclosure may further include a distance sensor 160, and the processor 140 according to an embodiment may identify, based on a plurality of sterilization areas 810, 820, and 830 being identified, a direction and distance of the respective sterilization areas using the distance sensor 160, and set a traveling route 300 for a sterilization operation based on the identified direction and distance. Here, the distance sensor 160 may be implemented as a Light Detection And Ranging (LIDAR) sensor.

Specifically, the processor 140 may identify angles measured from the reference line 800 is a clockwise direction as directions to the respective sterilization areas, and identify distances from the position of the robot 100 to the respective sterilization points included in the respective sterilization areas as distances to the respective sterilization areas.

Referring to FIG. 8, the processor 140 may identify a direction of a first sterilization area 810 as 80 degrees 811, and a distance as 20 meters 812. In addition, the processor 140 may identify a direction of a second sterilization area 820 as 120 degrees 821, and a distance as 30 meters 822. Lastly, the processor 140 may identify a direction of a third sterilization area 830 as 160 degrees 831, and a distance as 15 meters 832.

The processor 140 according to an embodiment of the disclosure may set a traveling route according to a pre-set method based on the directions and distances of the identified first to third sterilization areas. In FIG. 8, the traveling route 300 being set according to a method of prioritizing the sterilizing of a sterilization area which has a low angle value that corresponds to the identified direction for the respective sterilization areas is shown.

Specifically, the processor 140 may set the traveling route 300 of the robot 100 in an order of sterilizing the first sterilization area as top priority because the direction of the first sterilization area is closest with the reference line 800, then the second sterilization area, and lastly sterilizing the third sterilization area which is positioned at a direction farthest from the reference line 800.

However, the method of setting the traveling route described in FIG. 8 is merely one example, and the processor 140 may set the traveling route according to any other method. According to the various embodiments of the disclosure, in the case the robot 100 is a guide bot or a retail bot arranged in an indoor space in which many people are active, there is an advantage of being able to quickly and effectively sterilize the plurality of sterilization areas.

According to an embodiment, the robot 100 may further include a display which includes a touchscreen when the robot 100 is a guide bot or a retail bot, and the robot 100 may sterilize the display on its own when a pre-set time is passed after a touch operation of the user is input.

Figure 9:
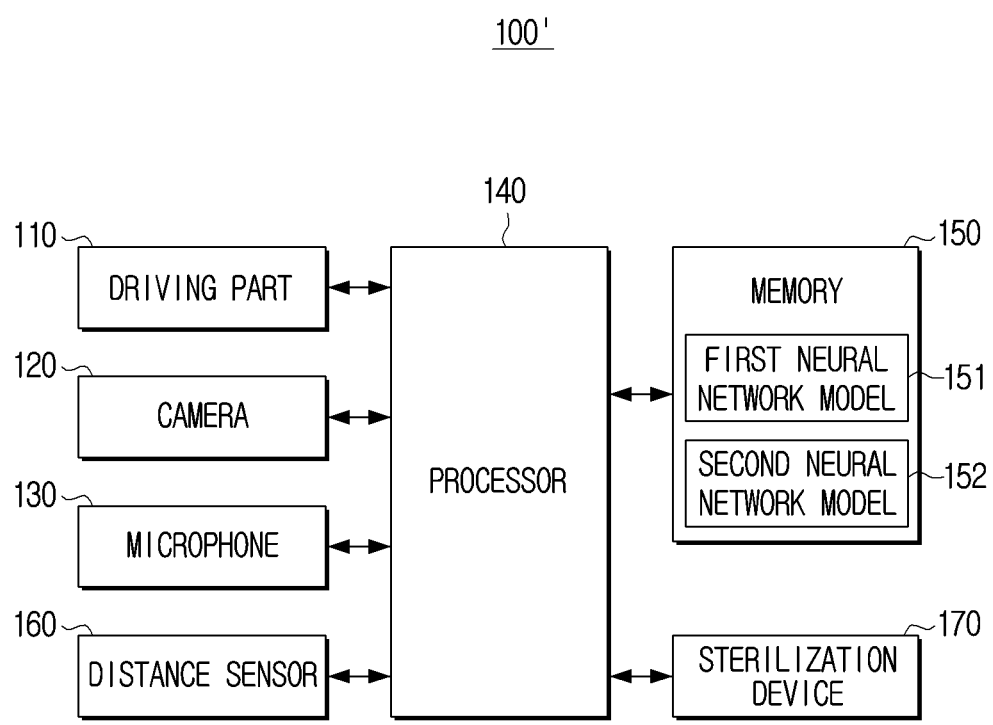
FIG. 9 is a block diagram illustrating a functional configuration of a robot according to an embodiment.

FIG. 9 is a block diagram illustrating a functional configuration of a robot according to an embodiment of the disclosure.

Referring to FIG. 9, a robot 100' may include the driving part 110, the camera 120, the microphone 130, the processor 140, the memory 150, a distance sensor 160, and a sterilization device 170. The detailed description of configurations shown in FIG. 9 that overlap with the configurations shown in FIG. 2 will be omitted.

The memory 150 may store data necessary for the various embodiments of the disclosure. The memory 150 may be implemented in a memory form embedded to the robot or implemented in a memory form attachable or detachable to the robot 100 according to a data storage use. For example, data for driving the robot 100 may be stored in the memory embedded to the robot 100, and data for an expansion function of the robot 100 may be stored in the memory attachable or detachable to the robot 100. The memory embedded in the robot 100 may be implemented as at least one of a volatile memory (e.g., a dynamic RAM (DRAM), a static RAM (SRAM), or a synchronous dynamic RAM (SDRAM)), or a non-volatile memory (e.g., one time programmable ROM (OTPROM), programmable ROM (PROM), erasable and programmable ROM (EPROM), electrically erasable and programmable ROM (EEPROM), mask ROM, flash ROM, a flash memory (e.g., NAND flash or NOR flash), a hard disk drive (HDD) or a solid state drive (SSD)). The memory attachable/detachable to the robot 100 may be implemented in a form such as, for example, and without limitation, a memory card (e.g., a compact flash (CF), a secure digital (SD), a micro secure digital (micro-SD), a mini secure digital (mini-SD), an extreme digital (xD), a multi-media card (MMC), etc.), an external memory (e.g., USB memory) connectable to a USB port, or the like.

In an example, the memory 150 may store at least one instruction or a computer program which includes the instructions for controlling the robot 100.

In another example, the memory 150 may store information associated with a neural network model that includes a plurality of layers. Here, the storing information associated with the neural network model may mean storing various information associated with an operation of the neural network model, for example, information on the plurality of layers included in the neural network model, information on parameters (e.g., filter coefficient, bias, etc.) used in the respective layers, and the like. For example, the memory 150 may store information on a first neural network model 151 trained to identify whether an input audio signal includes a coughing sound and a second neural network model 152 trained to identify whether non-mask wearing users are included in an obtained image according to an embodiment.

The distance sensor 160 may be a configuration for measuring a distance between the robot 100 and a sterilization point at which the coughing event occurred. The distance sensor 160 may be implemented as a Light Detection And Ranging (LIDAR) sensor, a depth camera, or the like. The distance sensor 160 according to an example may measure a distance between the robot 100 and a sterilization point through a triangulation method, a Time of Flight (ToF) measurement method, or a phase difference variation measurement method.

The sterilization device 170 may perform a function of killing viruses and bacteria when the robot 100 arrives at a sterilization area and performs a sterilization function. According to an example, the sterilization device 170 may be configured as a disinfecting solution spraying module which includes a tank in which the disinfecting solution is contained, a pipe through which the disinfecting solution flows, and a nozzle part which sprays the disinfecting solution.

According to another example, the sterilization device 170 may be implemented as an ultraviolet (UV) sterilization device which includes LEDs that can irradiate UV light. The sterilization device 170 may not only sterilize the sterilization area, but also perform a function of sterilizing the display included in the robot 100.

Figure 10:
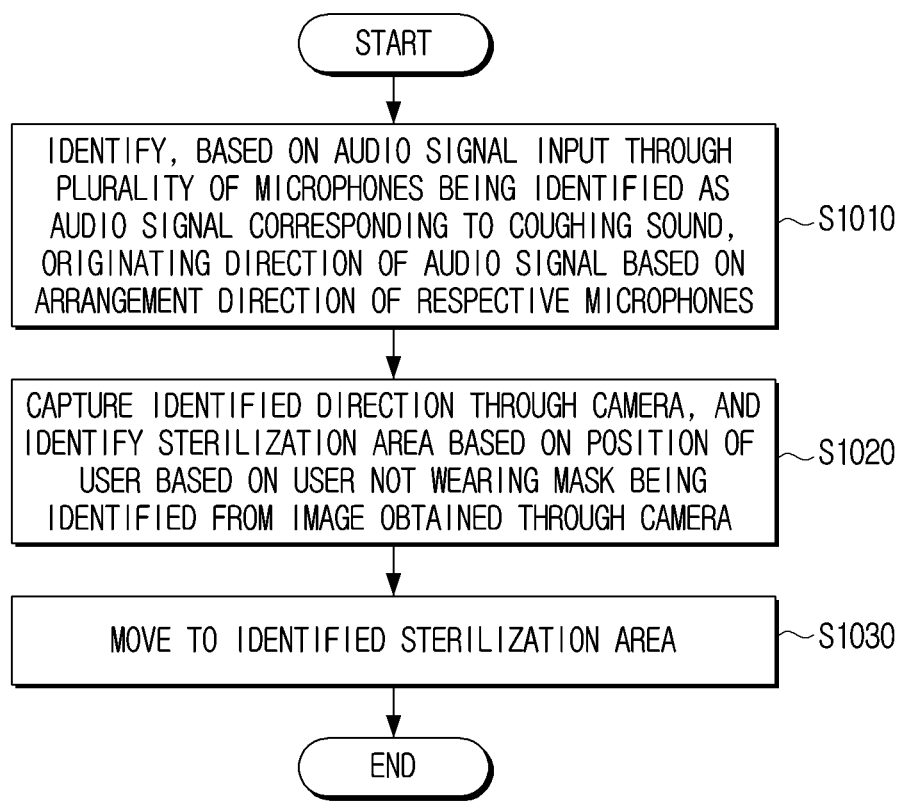
FIG. 10 is a flowchart illustrating a control method according to an embodiment.

FIG. 10 is a flowchart illustrating a control method according to an embodiment of the disclosure.

A control method of a robot according to an embodiment of the disclosure may include identifying, based on an audio signal input through the plurality of microphones being identified as an audio signal corresponding to a coughing sound, an originating direction of the audio signal based on an arrangement direction of the respective microphones (S1010). Then, the identified direction is captured through the camera, and a sterilization area is identified based on a position of a user based on a non-mask wearing user being identified from the image obtained through the camera (S1020). Lastly, the robot is configured to move to the identified sterilization area (S1030).

Here, the identifying the sterilization area (S1020) may include identifying an area of a threshold range based on a position of the user as the sterilization area based on an intensity of the audio signal.

In addition, the identifying the sterilization area (S1020) may include determining a scale of the sterilization area based on a number of non-mask wearing users.

In addition, the identifying the sterilization area (S1020) may include identifying, based on a plurality of non-mask wearing users being identified, a sterilization area based on the positions of the respective users.

In addition, the identifying the sterilization area (S1020) may include determining at least one of the scale of the sterilization area or the sterilization intensity based on whether the identified position of the user is within a pre-set area.

Here, the pre-set area may include at least one of an area in which an object with high contact frequency by users is positioned, an area with high visiting frequency by users, or an area with low mask wearing frequency by users.

The identifying the direction from which the audio signal is originated (S1010) may include identifying whether the input audio signal is the audio signal corresponding to the coughing sound by using the first neural network model, and the first neural network model may be a model trained to identify whether the input audio signal includes the coughing sound.

The identifying the sterilization area (S1020) may include identifying whether the obtained image includes non-mask wearing users by using a second neural network model, and the second neural network model may be a model trained to identify whether non-mask wearing users are included in the obtained image.

In addition, the method may further include identifying, based on a plurality of sterilization areas being identified, a direction and distance of the respective sterilization areas and setting a traveling route for a sterilization operation based on the identified direction and distance.

The method may further include performing the sterilization function when the robot is moved to the identified sterilization area.

The methods according to the various embodiments of the disclosure described above may be implemented in an application form installable in a robot of related art.

In addition, the methods according to the various embodiments of the disclosure described above may be implemented by a software upgrade for the robot of the related art or with only a hardware upgrade.

In addition, the various embodiments of the disclosure described above may be performed through an embedded server included in the robot, or at least one external server.

The various embodiments described above may be implemented in a recordable medium which is readable by a computer or a device similar to the computer using a software, a hardware, or a combination of the software and hardware. In some cases, embodiments described herein may be implemented by the processor 140 itself. According to a software implementation, embodiments such as the procedures and functions described herein may be implemented with separate software modules. The respective software modules may perform one or more functions and operations described herein.

The computer instructions for performing processing operations of the robot 100 according to the various embodiments described above may be stored in a non-transitory computer-readable medium. The computer instructions stored in this non-transitory computer-readable medium may cause a specific device to perform a processing operation of the robot 100 according to the above-described various embodiments when executed by a processor of the specific device.

The non-transitory computer readable medium may refer to a medium that stores data semi-permanently rather than storing data for a very short time, such as a register, a cache, a memory, or the like, and is readable by a device. Specific examples of the non-transitory computer readable medium may include, for example, and without limitation, a compact disc (CD), a digital versatile disc (DVD), a hard disc, a Blu-ray disc, a USB, a memory card, a ROM, and the like.

While the disclosure has been illustrated and described with reference to various example embodiments thereof, it will be understood that the various example embodiments are intended to be illustrative, not limiting. It will be understood by those skilled in the art that various changes in form and details may be made therein without departing from the true spirit and full scope of the disclosure, including the appended claims and their equivalents.

What is claimed is:

1. A method of controlling a robot comprising:
identifying that an audio signal input through a plurality of microphones on the robot corresponds to a coughing sound,
based on the audio signal input through the plurality of microphones on the robot being identified as corresponding to the coughing sound, identifying an originating direction of the audio signal based on an arrangement direction of each microphone and a difference in intensity of audio signals that are respectively input to the plurality of microphones, wherein the plurality of microphones are arranged in different directions;
based on the audio signal input through the plurality of microphones being identified as corresponding to the coughing sound, capturing an image in the originating direction of the audio signal corresponding to the coughing sound using a camera on the robot;
identifying a sterilization area based on a position of a non-mask wearing user identified from the image; and
moving the robot to the sterilization area.

2. The method of claim 1, wherein identifying the sterilization area comprises:
identifying the sterilization area based on the position of the non-mask wearing user and a threshold range corresponding to an intensity of the audio signal.

3. The method of claim 1, wherein identifying the sterilization area comprises:
determining a scale of the sterilization area based on a number of non-mask wearing users identified from the image.

4. The method of claim 1, wherein identifying the sterilization area comprises:
identifying the sterilization area based on a plurality of positions corresponding to a plurality of non-mask wearing users identified from the image.

5. The method of claim 1, wherein identifying the sterilization area comprises:
determining at least one of a scale of the sterilization area and a sterilization intensity, based on whether the position of the non-mask wearing user is within a pre-set area.

6. A non-transitory computer readable medium for storing computer readable program code or instructions which are executable by a processor to perform a method of controlling a robot, the method comprising:
based on an audio signal input through a plurality of microphones on the robot being identified as corresponding to a coughing sound, identifying an originating direction of the audio signal based on an arrangement direction of each microphone and a difference in intensity of audio signals that are respectively input to the plurality of microphones, wherein the plurality of microphones are arranged in different directions;
based on the audio signal input through the plurality of microphones being identified as corresponding to the coughing sound, capturing an image in the originating direction of the audio signal corresponding to the coughing sound using a camera on the robot;
identifying a sterilization area based on a position of a non-mask wearing user identified from the image; and
moving the robot to the sterilization area.

7. The non-transitory computer readable medium of claim 6, wherein identifying the sterilization area comprises:
identifying the sterilization area based on the position of the non-mask wearing user and a threshold range corresponding to an intensity of the audio signal.

8. The non-transitory computer readable medium of claim 6, wherein identifying the sterilization area comprises:
determining a scale of the sterilization area based on a number of non-mask wearing users identified from the image.

9. The non-transitory computer readable medium of claim 6, wherein identifying the sterilization area comprises:
identifying the sterilization area based on a plurality of positions corresponding to a plurality of non-mask wearing users identified from the image.

10. The non-transitory computer readable medium of claim 6, wherein identifying the sterilization area comprises:
determining at least one of a scale of the sterilization area and a sterilization intensity, based on whether the position of the non-mask wearing user is within a pre-set area.

11. A robot, comprising:
a driving part;
a camera;
a plurality of microphones arranged in different directions;
a memory storing instructions; and
a processor configured to execute the instructions to:
based on an audio signal input through the plurality of microphones being identified as corresponding to a coughing sound, identify an originating direction of the audio signal based on a difference in intensity of audio signals that are respectively input to the plurality of microphones arranged in different directions,
based on the audio signal input through the plurality of microphones being identified as corresponding to the coughing sound, control the camera to capture an image in the originating direction of the audio signal corresponding to the coughing sound,
identify a sterilization area based on a position of a non-mask wearing user identified from the image, and
control the driving part to move to the sterilization area.

12. The robot of claim 11, wherein the processor is further configured to execute the instructions to:
identify the sterilization area based on the position of the non-mask wearing user and a threshold range corresponding to an intensity of the audio signal.

13. The robot of claim 11, wherein the processor is further configured to execute the instructions to:
determine a scale of the sterilization area based on a number of non-mask wearing users identified from the image.

14. The robot of claim 11, wherein the processor is further configured to execute the instructions to:
identify the sterilization area based on a plurality of positions corresponding to a plurality of non-mask wearing users identified from the image.

15. The robot of claim 11, wherein the processor is further configured to execute the instructions to:
determine at least one of a scale of the sterilization area, area and a sterilization intensity, based on whether the position of the non-mask wearing user is within a pre-set area.

16. The robot of claim 15, wherein the pre-set area comprises at least one of an area including an object with high contact frequency by users, an area with high visiting frequency by users, and an area with low mask wearing frequency by users.

17. The robot of claim 11, wherein the processor is further configured to execute the instructions to:
identify whether the audio signal corresponds to the coughing sound by using a first neural network model trained to identify whether the audio signal comprises a coughing sound.

18. The robot of claim 11, wherein the processor is further configured to execute the instructions to:
identify whether the image comprises the non-mask wearing user by using a neural network model trained to identify whether the image comprises a non-mask wearing user.

19. The robot of claim 11, further comprising:
a distance sensor,
wherein the processor is further configured to execute the instructions to:

based on a plurality of sterilization areas being identified, identify a direction and a distance with respect to each sterilization area using the distance sensor, and set a traveling route for a sterilization operation based on the direction and distance to each sterilization area.

20. The robot of claim 11, further comprising:

a sterilization device configured to perform a sterilization function, wherein the processor is further configured to execute the instructions to:

control the sterilization device to perform the sterilization function, based on the robot having moved to the sterilization area.

21. The robot of claim 11, wherein the processor is further configured to execute the instructions to:

control the camera to capture an image of a space in which the robot is positioned, identify a ratio of users who are wearing a mask among users in the image, identify the sterilization area as an area in which a ratio of non-mask wearing people exceeds a threshold ratio.

\* \* \* \* \*